United States Patent
Balagere et al.

(10) Patent No.: US 9,773,094 B1
(45) Date of Patent: Sep. 26, 2017

(54) METHODS AND SYSTEMS FOR PHARMACY MODELING

(71) Applicant: Express Scripts, Inc., St. Louis, MO (US)

(72) Inventors: Dhanur S. Balagere, St. Louis, MO (US); David A. Tomala, Chesterfield, MO (US); Robert F. Nease, St. Louis, MO (US); Reethi N. Iyengar, St. Louis, MO (US)

(73) Assignee: Express Scripts, Inc., St. Louis, MO (US)

( * ) Notice: Subject to any disclaimer, the term of this patent is extended or adjusted under 35 U.S.C. 154(b) by 436 days.

(21) Appl. No.: 14/612,005

(22) Filed: Feb. 2, 2015

Related U.S. Application Data

(60) Provisional application No. 61/934,133, filed on Jan. 31, 2014.

(51) Int. Cl.
  *G06F 17/00* (2006.01)
  *G06N 5/02* (2006.01)
  *G06F 19/00* (2011.01)
  *G06F 17/50* (2006.01)

(52) U.S. Cl.
  CPC ...... *G06F 19/3437* (2013.01); *G06F 17/5009* (2013.01)

(58) Field of Classification Search
  CPC combination set(s) only.
  See application file for complete search history.

(56) References Cited

U.S. PATENT DOCUMENTS

| | | | | |
|---|---|---|---|---|
| 7,813,953 B2* | 10/2010 | Boardman | ............ | G06Q 10/06 705/7.31 |
| 7,877,277 B1 | 1/2011 | Petit et al. | | |
| 8,498,891 B2* | 7/2013 | Boardman | ............ | G06Q 10/06 705/7.31 |
| 8,666,926 B1* | 3/2014 | Nease | ................ | G06F 19/3456 705/2 |
| 8,799,030 B1* | 8/2014 | Chen | .................... | G06F 19/322 705/4 |

(Continued)

OTHER PUBLICATIONS

Simulation Model to Predict Failure Cycles in Board Level Drop Test Wei Wang; Daniel Robbins; Christopher Glancey 2016 IEEE 66th Electronic Components and Technology Conference (ECTC) Year: 2016 pp. 1886-1891, DOI: 10.1109/ECTC.2016.393 IEEE Conference Publications.*

(Continued)

*Primary Examiner* — Michael B Holmes
(74) *Attorney, Agent, or Firm* — Husch Blackwell LLP

(57) ABSTRACT

Methods and systems for pharmacy modeling are described. The risk adjusted pharmacy predictive model is created from member data, claims data, and population data. This model can be used to compare the actual pharmacy performance to an expected actual pharmacy performance value, which can be used to identify pharmacies at risk or not performing to an acceptable level. The model can be used for adherence and generic drug utilization ratings of pharmacies. The pharmacy can be judged on a therapy class by therapy class basis with factors that reflect the demographic, socio-economic, location, benefits attributes, etc. that actually affect the performance of the pharmacy and may assist in determining the quality of care by a pharmacy.

18 Claims, 5 Drawing Sheets

(56) References Cited

U.S. PATENT DOCUMENTS

| | | | |
|---|---|---|---|
| 9,147,163 B1* | 9/2015 | Nease | G06F 19/3456 |
| 9,196,172 B1* | 11/2015 | Miller | G09B 19/0092 |
| 2008/0177567 A1 | 7/2008 | Friedlander et al. | |
| 2015/0032465 A1* | 1/2015 | Sundar | G06F 19/3481 |
| | | | 705/2 |

OTHER PUBLICATIONS

Statewide validation of a patient admissions prediction tool Justin Boyle; Remy Le Padellec; Derek Ireland 2010 Annual International Conference of the IEEE Engineering in Medicine and Biology Year: 2010 pp. 3887-3890, DOI: 10.1109/IEMBS.2010.5627673 IEEE Conference Publications.*

Dye Concentrations Measurement Using Mach-Zehner Interferometer Sensor and Modeled by ANFIS Su Sin Chong; Abdul Aziz Bin Abdul Raman; Sulaiman W. Harun; Hamzah Arof IEEE Sensors Journal Year: 2016, vol. 16, Issue: 22 pp. 8044-8050, DOI: 10.1109/JSEN.2016.2607753 IEEE Journals & Magazines.*

Prediction of glioblastoma multiforme response to bevacizumab treatment using diffusion and perfusion imaging Ehsan Abadi; Hamid Soltanian-Zadeh; Lisa Scarpace; Tom Mikkelsen 2015 22nd Iranian Conference on Biomedical Engineering (ICBME) Year: 2015 pp. 314-318, DOI: 10.1109/ICBME.2015.7404162 IEEE Conference Publications.*

* cited by examiner

METHODS AND SYSTEMS FOR PHARMACY MODELING

CROSS-REFERENCE TO A RELATED APPLICATION

This application claims the benefit of U.S. Provisional Patent Application No. 61/934,133, filed on 31 Jan. 2014, titled "Methods and Systems for Risk Adjustment Pharmacy Modeling," the entire disclosure of which is incorporated herein by reference.

FIELD

The field relates to predictive modeling, and more specifically to predictive modeling using pharmacy data including drug claims data and non-claims pharmacy data.

DETAILED DESCRIPTION

Figure 1:
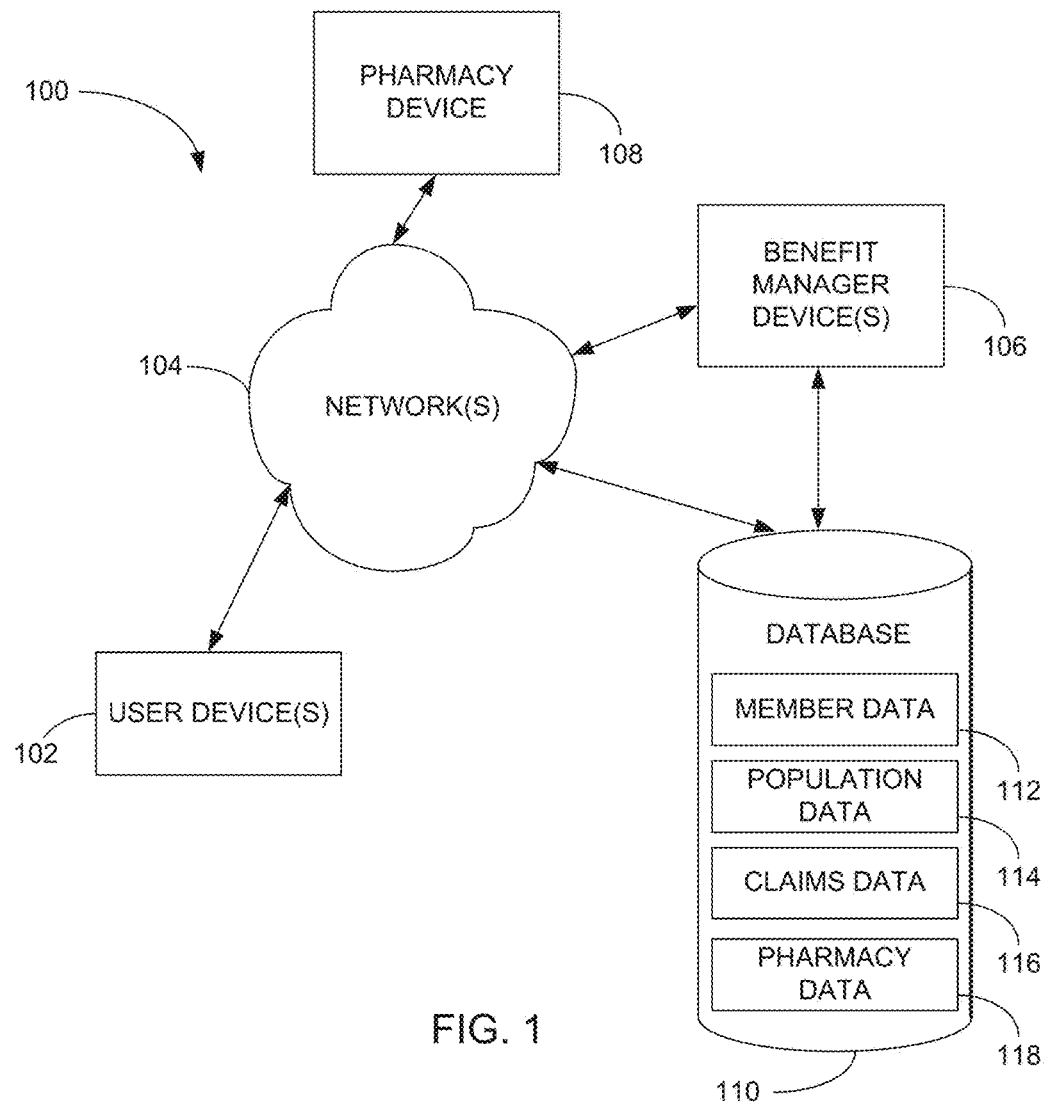
FIG. 1 is a block diagram of an example system, according to an example embodiment.

Example methods and systems for pharmacy modeling are described. The models can be used to determine quality of care provided by the pharmacy or value provided by the pharmacy, e.g., clinical quality of a retail pharmacy. In the following description, for purposes of explanation, numerous specific details are set forth in order to provide a thorough understanding of example embodiments. It will be evident, however, to one of ordinary skill in the art that embodiments of the invention may be practiced without these specific details.

The Centers for Medicare and Medicaid Services ("CMS") has established a quality rating system to help consumers, their families, and caregivers compare nursing homes more easily and to help identify areas about which a consumer may want to ask questions. CMS has extended the star rating system to drug plans. Measuring quality in the pharmacy network for health plans may be performed to, among other things, improve star ratings.

Pharmacy quality measures can be explicitly defined and measured with relative accuracy using pharmacy claims data. The methods and systems may enable measures that improve accuracy. For example, the improved measures adjust for factors that are beyond the control of the pharmacies such as demographics of patients serviced, plan design factors, prior authorizations, and the like. The methods and systems provide a methodology to empirically adjust the pharmacy quality measure that eliminates the influence of factors that are beyond the control of individual pharmacies. That is, the methods and systems take into account indirect factors that are beyond the control of the pharmacy to better indicate the pharmacy quality measure. Factors can be data related to a pharmacy, e.g., member data, claims data, and population data.

In some embodiments, a pharmacy model may be used to determine a standard to which pharmacies can be held for the adherence, or improving the adherence, for an associated pharmacy patient population. Other standards that can be measured using the present disclosure include generic dispensing ratio. Each of these models can be determined using a heuristic system that begins with numerous factors available to the system. These factors relate to the pharmacy but may be directed to the demographic and socioeconomic attributes of the members (e.g., patients being served by the pharmacy), pharmacy benefit design attributes, location attributes, and therapy class. The methods and systems reduce these factors to only those factors that influence the actual performance of the pharmacy.

In some embodiments, a pharmacy model may be developed using dimension reduction techniques and/or a heuristic process. While a large number of initial variables may be considered (e.g., around 300 variables), a lesser number may be selected and then a variable selection technique (e.g., PROC GLMSELECT) may be used to further select appropriate variables to include in the predictive model. That is, variables that are predictive of pharmacy performance are distilled from the three hundred plus variables to a number of variables that can be more efficiently processed. The variable reduction process can be performed in multiple steps, e.g., two, three or four steps, with variables being removed at each stage. The stages may each use a different technique to determine if a variable remains in the model or is removed from the model.

In some embodiments, the pharmacy model may compute a percentage of patients of a particular pharmacy that are expected to be adherent. This percentage may be compared against the actual percentage of patients of the pharmacy that are adherent.

In some embodiments, the pharmacy model may compute an expected generic dispensing ratio of a particular pharmacy. This calculated, expected ratio may then be compared against the actual generic dispensing ratio of the pharmacy.

FIG. 1 is a block diagram of an example system 100, according to an example embodiment. The system 100 includes a user device 102 in communication with a benefit manager device 106 and/or a pharmacy device 108 over a network 104.

The user device 102 is used by a device operator. The user device 102 may be a stand-alone device that solely provides at least some of the functionality to enable pharmacy modeling.

Examples of the devices 102, 106, 108 include a processing circuitry, a set-top box (STB), a receiver card, a mobile telephone, a personal digital assistant (PDA), a display device, a portable gaming unit, and a computing system; however other devices for modelling and using a model may also be used. For example, the user device 102 may include a mobile electronic device, such an IPHONE or IPAD device by Apple, Inc., mobile electronic devices powered by ANDROID by Google, Inc., and a BLACKBERRY device by Research In Motion Limited. The user device 102 also include other computing devices, such as desktop computing devices, notebook computing devices, netbook computing devices, gaming devices, and the like. Other types of electronic devices may also be used. Each of these devices includes circuitry that exemplifies a dedicated computing device when performing any of the processes described herein.

The network 104 by which one or more than one of the devices 102, 106, 108 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may also include optical communications. Wireless communications include a broadcast signal embodying information through the air or a directed signal also through the air. Other conventional and/or later developed wired and wireless networks may also be used. In some embodiments, the network 104 may include proprietary network communication technologies such as secure socket layers (SSL) technology, technology found in a prescribing network (e.g., the electronic prescribing network operated by Surescripts of Arlington, Va.), and the like.

The benefit manager device 106 is a device operated by an entity at least partially responsible for the management of a drug benefit program. While the entity operating the benefit manager device 106 is typically a pharmacy benefits manager ("PBM"), other entities may operate the benefit manager device 106 either on behalf of themselves, the PBM, or another entity.

Some of the operations of the PBM that operates the benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location. A member is a patient that is entitled to a pharmacy benefit.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

In conjunction with receiving the co-pay (if any) from the member and dispensing the prescription drug to the member, the pharmacy submits a claim to the PBM for the prescription drug. The PBM may perform certain adjudication functions including verifying the eligibility of the member, reviewing the formulary to determine appropriate co-pay, coinsurance, and deductible for the prescription drug, and performing a drug utilization review (DUR) on the member. The PBM then adjudicates the claim associated with the prescription drug and provides a response to the pharmacy following performance of the aforementioned functions. As part of the adjudication, the client (or the PBM on behalf of the client) ultimately reimburses the pharmacy for filling the prescription drug when the prescription drug was successfully adjudicated. The aforementioned adjudication functions generally occur before the co-pay is received and the prescription drug dispensed. However, the operations may occur simultaneously, substantially simultaneously, or in a different order. In addition, more or less adjudication functions may be performed as part of the adjudication process. Certain adjudications, payments and business relationship between the pharmacy and the PBM may depend in part on the calculated quality of the pharmacy using the model.

The pharmacy device 102 may include pharmacy hardware and/or software of to enable the pharmacy (e.g., a mail order pharmacy and/or or a retail pharmacy) to fulfill prescription drug orders. The pharmacy device 102 may be operated in an automated manner as directed by an operator (e.g., a pharmacist or pharmacist technician), manually (e.g., by a pharmacist or pharmacist technician), or otherwise. Examples of pharmacy operations that may be performed by pharmacy device 102 include filling a prescription after removing pharmaceuticals from inventory, labeling a container with prescription information, filling a container, blister pack, or other packaging with the pharmaceutical, verifying the type and quantity of the pharmaceutical in the container with that which is printed on the label, capping or otherwise closing the packaging, preparing the packaging for shipment or other delivery to a patient associated with the prescription, and the like.

In some embodiments, the pharmacy device 108 may be a device associated with a retail pharmacy location (e.g., an independent pharmacy or a pharmacy location of a local or national chain such as WALGREENS, DUANE REED or CVS), a grocery store with a retail pharmacy (e.g., an independent grocery store or a grocery store location of a local or national chain such as ALDI, KROGERS, or SCHNUCKS) or a general sales store with a retail pharmacy (e.g., an independent general sales store or a store location of a local or national chain such as WALMART or TARGET) or other type of pharmacy location at which a member attempts to obtain a prescription. In some embodiments, the pharmacy device 108 may be utilized to submit the claim to the PBM for adjudication. Additionally, in some embodiments, the pharmacy device 108 may enable information exchange between the pharmacy and the PBM, for example, to allow the sharing of member information such as drug history, and the like, that may allow the pharmacy to better service a member (e.g., by providing more informed therapy consultation and drug interaction information, etc.). This member information may also be used in determining a pharmacy model or determining pharmacy quality using the pharmacy model.

In some embodiments, the pharmacy device 108 may be associated with a mail order pharmacy. The mail order pharmacy may fill or refill the prescription, and may deliver the prescription drug to the member via a parcel service in accordance with an anticipated need, such as a time-wise schedule, or the like. As such, the member may not need to visit the retail pharmacy store in person to have the prescription refilled and/or to pick up the refilled prescription. In addition to the convenience of receiving the refills of the prescription directly to the member's home or other designated location of delivery, the cost of the prescription drugs purchased through a mail order delivery pharmacy may be less than the cost of the same prescription drugs purchased from a retail pharmacy. The lower costs available through the mail order pharmacy may be the result, for example, of economies available to the mail order pharmacy that may be at least partially passed along to the member as well as the savings realized by the client. The lower costs available through the mail order pharmacy may be the result of a lower co-pay required by the member according to a health care plan, under which the member may receive the prescription drugs. The pharmacy device 108 may communicate with the benefit manager device 106 in a similar manner as described above. This information associated with the mail order pharmacy may also be used in determining a pharmacy model or determining pharmacy quality using the pharmacy model.

The user device 102 may be in a client-server relationship with the devices 106, 108 a peer-to-peer relationship with the devices 106, 108, and/or in a different type of relationship with the devices 106, 108.

The benefit manager device 106 may be in communication directly (e.g., through local storage) and/or through the network 104 (e.g., in a cloud configuration or software as a service) with a database 110. The database 110 may be deployed on the user device 102, the benefit manager device 106, both the user device 102 and the benefit manager device 106, partially on the user device 102 and partially on the benefit manager device 106, on a separate device, or may otherwise be deployed. The database 110 may store member data 112, population data 114, claims data 116, and/or pharmacy data 118.

The member data 112 includes information regarding the members associated with the benefit manager. Examples of the member data 112 include name, address, telephone number, e-mail address, prescription drug history, and the like. The member data 112 may include a plan sponsor identifier that identifies the plan sponsor associated with the member and/or a member identifier that identifies the member to the plan sponsor. The member data 112 may include a member identifier that identifies the plan sponsor associated with the patient and/or a patient identifier that identifies the patient to the plan sponsor. The member data 112 may also include, by way of example, dispensation preferences such as type of label, type of cap, message preferences, language preferences, or the like. The member data 112 may be accessed by various devices in the pharmacy to obtain information utilized for fulfillment and shipping of prescription orders.

In some embodiments, the member data 112 may include information for persons who are patients of the pharmacy but are not members in a benefit plan being provided by the benefit manager. For example, these patients may obtain drug directly from the pharmacy, through a private label service offered by the pharmacy, or otherwise. In general, the use of the terms member and patient may be used interchangeably herein.

Population data 114 includes information about persons residing in various geographic areas. For example, the population data 114 may include a postal code, e.g., ZIP code level, U.S. Census data (www.census.gov). The geographic area can also be defined by counties, city, town, or other political boundaries. The population data may also include pharmacy benefit manager device defined geographic areas, e.g., associating member by the pharmacy that the member normally uses, e.g., a pharmacy close to a member's work location instead of a home location. This pharmacy location information may be used in determining a pharmacy model or determining pharmacy quality using the pharmacy model.

The claims data 116 includes information regarding pharmacy claims adjudicated by the PBM under a drug benefit program provided by the PBM for one, or more than one, clients. In general, the claims data 116 may include client data (e.g., including an identification of the client that sponsors the drug benefit program under which the claim is made, company name, company address, contact name, contact telephone number, contact email address, and the like), an identification of the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. The claims data 116 may also include claims adjudicated for healthcare related services other than prescriptions filled under a drug benefit program. Examples of other healthcare related services may include medical services (such as treatment, screening services, and laboratory services), dental related services, and vision care related services. Additional information may be included in the various claims of the claims data 116. The claims data 116 may also be used in determining a pharmacy model or determining pharmacy quality using the pharmacy model.

The pharmacy data 118 may include information regarding pharmacies. The pharmacy data 118 may include, by way of example, national provider identifier information associated with the pharmacies, location data regarding the location of the pharmacies, information data regarding the pharmacy hours and/or telephone number, pharmacy network association data defining the pharmacy network associations of which the pharmacies are associated, and the like. The pharmacy data 118 may be used in determining a pharmacy model or determining pharmacy quality using the pharmacy model.

While the system 100 in FIG. 1 is shown to include single devices 102, 106, 108 multiple devices may be used. The devices 102, 106, 108 may be the same type of device or may be different device types. When multiple devices are present, the multiple devices may be of the same device type or may be a different device type. Moreover, system 100 shows a single network 104; however, multiple networks can be used. The multiple networks may communicate in series with each other to link the devices 102, 106, 108 or in parallel to link the devices 102, 106, 108. When determining a pharmacy model or determining pharmacy quality these devices 102, 106, 108 may perform the determination method either alone or in combination(s).

Figure 2:
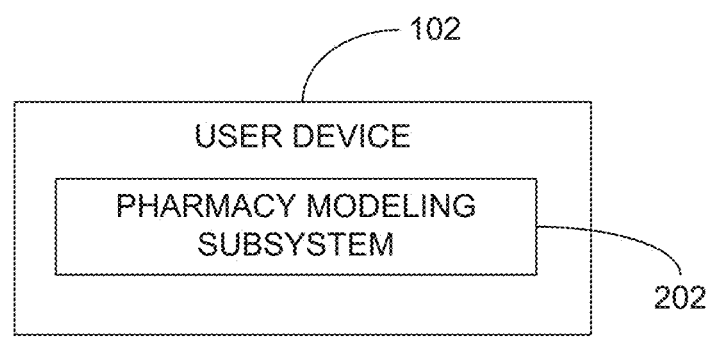
FIG. 2 is a block diagram of an example user device that may be deployed within the system of FIG. 1, according to an example embodiment.

FIG. 2 illustrates the user device 102, according to an example embodiment. The user device 102 may be used by a device operator to perform risk adjustment pharmacy modeling. The user device 102 may be deployed in the system 100, or may otherwise be used.

The user device 102 may include a pharmacy modeling subsystem 202. In some embodiments, the pharmacy modeling subsystem 202 may enable a risk adjustment predictive model to be generated and/or used.

Figure 3:
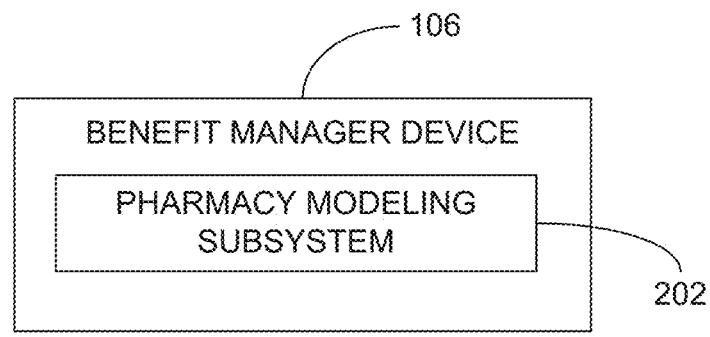
FIG. 3 is a block diagram of an example benefit manager device that may be deployed within the system of FIG. 1, according to an example embodiment.

FIG. 3 illustrates the benefit manager device 106, according to an example embodiment. The benefit manager device 106 may be used by a device operator to perform risk adjustment pharmacy modeling. The benefit manager device 106 may be deployed in the system 100, or may otherwise be used.

The benefit manager device 106 may include the pharmacy modeling subsystem 202. In some embodiments, the pharmacy modeling subsystem 202 when used may provide server-side functionality to the user device 102. By way of example, the pharmacy modeling subsystem 202 may be deployed in both the user device 102 and the benefit manager device 106. The user device 102 may then perform some of the functionality while other functionality is performed by the benefit manager device 106.

The pharmacy modeling subsystem 202 may be used to analyze pharmacy quality measures. In some embodiments, a method or study may be used as at least part of the analysis. Example methods are described below.

Figure 4:
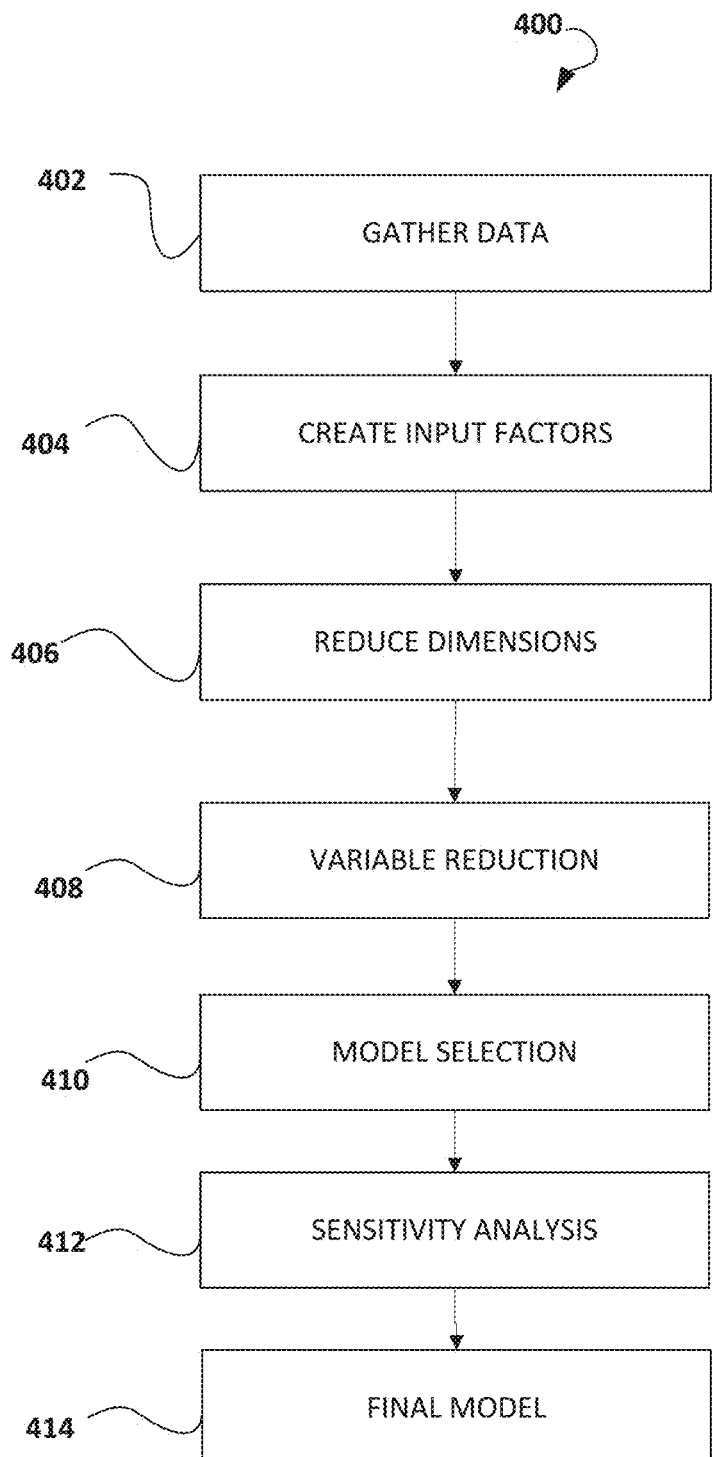
FIG. 4 is a process flow illustrating a method of generating a predictive model, according to an example embodiment.

FIG. 4 shows a method 400 for using the methods and systems described herein to evaluate a pharmacy or drug dispenser to determine a true risk and performance of the pharmacy. The present method uses large data sets to determine the performance of the pharmacy by using data available to a pharmacy organization, e.g., a pharmacy benefits manager, along with data from other sources.

At block 402, data is gathered. The data can be gathered from various sources including analyzed and aggregate pharmacy claims data, patient demographic, and geographic data. This data can then be reformulated to be at a pharmacy level. That is, the data is associated to an individual pharmacy or an insured company. The data is not identified to an individual. The data can be from public databases or derived from private and public databases. Data can include member data 112, population data 114, and claims data 116. This gathered data may be all data that can be associated with a pharmacy, including patient demographic data, patient socioeconomic data, pharmacy benefit attributes, pharmacy location, patient characteristics at the pharmacy and therapy classes.

At block 404, the gathered data is transformed into factors that relate to an individual pharmacy. Examples include demographic attributes of patients serviced at the pharmacy. A factor can be pharmacy socio-economic attributes of patients serviced at the pharmacy. A factor can be pharmacy benefit design attributes of patients serviced at the pharmacy. A factor can be pharmacy location variables, e.g., U.S. census region, postal code, voting district, county, municipal area, city, state, congressional districts and the like. A factor can be therapy class variables, percent of claims dispensed by the pharmacy for each therapy class included in the present analysis. A therapy class can be a specialty therapy class, e.g., Inflammatory Conditions, Multiple Sclerosis, Cancer, HIV, Growth Deficiency, Miscellaneous CNS Disorders, Respiratory Conditions, Anticoagulants, Transplant, Pulmonary Hypertension and the like. A therapy class can be a traditional therapy, e.g., Diabetes, High Blood Cholesterol, High Blood Pressure/Heart Disease, Ulcer Disease, Asthma, Attention Disorders, Depression, Mental/Neurological Disorders, Pain, Infections and the like. Some therapies can be included; some therapies can be excluded.

At block 406, the number of dimensions of the factors is reduced. The factors that are determined based on data relating to the pharmacy can number in the hundreds, if not thousands. Such a large number of factors cannot be efficiently analyzed. At block 406, the large number of factors (e.g., input variables) is reduced into a subset of factors that contain the most information about the model. This process reduces data redundancy and keeps only the factors which contain strong signal, which will influence the calculated end value. An example of dimension reduction is principal component analysis. Principal component analysis is a multivariate technique for examining relationships among several quantitative variables. Principal component analysis detects linear relationships in the data and reduces the number of variables in regression modeling. As input principal component analysis can use raw data, a correlation matrix, a covariance matrix, or a sum-of-squares-and-crossproducts (SSCP) matrix. Principal component analysis creates output data sets containing eigenvalues, eigenvectors, and standardized or unstandardized principal component scores. Principal component analysis is a multivariate technique for examining relationships among several quantitative variables. Another example of dimension reduction is factor analysis. Factor analysis is a statistical method used to describe variability among observed, correlated variables in terms of a potentially lower number of unobserved variables.

At block 408, factors are further reduced using a variable reduction technique. A variable reduction technique is used to select the most relevant factors for the final regression modeling. A k-fold cross validation option within the procedure can be used to arrive at the list of important variables. A variable reduction technique can effect selection in the framework of general linear models. A variety of model selection methods can be used, e.g., GLMSELECT procedure from SAS, the LASSO method of Tibshirani (1996) and the related LAR method of Efron et al. (2004). The variable selection can customize the selection with a wide variety of selection and stopping criteria, from traditional and computationally efficient significance-level-based criteria to more computationally intensive validation-based criteria. These can be set to best operate on the gathered data and the pharmacy model factors.

After completing performance of the operations at blocks 406 and 408, the factors relating a pharmacy's quality, risk and/or performance are reduced by an order or magnitude or from thousands to ten to twenty factors that contain data that will determine a true performance metric of the pharmacy for a therapy, overall performance, etc.

At block 410, a model for the pharmacy is selected. The selection of the model is done using a statistical analysis, e.g., a STEPWISE regression method. Examples of stepwise regression can include stepwise regression includes regression models in which the choice of predictive variables is carried out by an automatic procedure, which can take the form of a sequence of F-tests or t-tests, but other techniques are possible, such as adjusted R-square, Akaike information criterion, Bayesian information criterion, Mallows's Cp, PRESS, or false discovery rate. The stepwise regression can include forward selection, backward elimination or bidirectional elimination. The stepwise regression introduces one variable at a time at every "step" and evaluates the model performance at that step. This approach allows the method 400 to arrive at the most optimal algorithm for the model with variables that contain the most amount of information. Note that the model selection is performed on the reduced factor set from block 408.

At block 412, a sensitivity analysis can be performed. The sensitivity analysis allows the outlying factors to be analyzed to determine if the outlying factors should be part of the model. Further, influential data points can be used to evaluate model robustness. Sensitivity analysis can quantify the uncertainty in any model results, e.g., uncertainty analysis. The sensitivity analysis can further evaluate how much each input is contributing to the output uncertainty. Sensitivity analysis can addresses these issues, performing the role of ordering by importance the strength and relevance of the inputs in determining the variation in the output. The sensitivity analysis can further account for computational expense in the pharmacy model.

At block 414, a final model is determined and the final model is used to determine the pharmacy performance, pharmacy quality or pharmacy risk. This final model will use more than ten factors and less than twenty-five factors. In an example, the factors for any given model are in the range of 16-20 factors. The final model includes the factors that affect the pharmacy performance for the pharmacy therapy class for which the model is being developed. The factors can also be assigned weights within the model. For example, in the development of a generic dispensing model, the method 400 has identified that demographic and socio-economic attributes of the members (patients) is a factor or factors, along with pharmacy benefits and location of the pharmacy being factors. However, location of the pharmacy may be of lesser importance to the model than some of the demographic and socio-economic factors, e.g., the percent of female patients at the pharmacy in the therapy class or average age of patients. Accordingly, a higher weight is given to the demographic and socio-economic factor than to the pharmacy location factor.

The method 400 can be executed on the subsystems 202 or the computing device of FIG. 6, which is described below. The method 400 can be executed to determine the statistical models using SAS 9.3 statistical software. Specifically, the SAS procedures PROC GLMSELECT may be used for dimensionality reduction and PROC REG with STEPWISE option may be used for model selection.

The method 400 takes a first set of factors, which can be quite large (e.g., in the hundreds or thousand factors), and reduces the first sect of factors through a series of iterations (e.g., blocks 406-412) to arrive at a final set of factors that influence the rating of the pharmacy for a particular therapy class. The method 400 removes redundant factors and factors that do not influence the end result of the pharmacy model.

The example method 400 may analyze two types of pharmacy quality measures at an individual pharmacy. The first one is the Generic Dispensing Rate (GDR), which is defined as the proportion of generic prescriptions divided by the total number of prescriptions. The second measure that may be analyzed relates to medication adherence. These two pharmacy quality measures are illustrative of the present methods and systems and the present disclosure is not limited to only GDR and adherence.

GDR is a pharmacy measure used in evaluating pharmacy benefit designs. A prescription drug plan with higher GDR means that the prescription drug costs are lower for members insured under the plan. Four separate measures may be analyzed (e.g., by the pharmacy modeling subsystem 202) at the pharmacy level. In some embodiments, these four measures may provide a good combination of cost and quality at a pharmacy, which are two factors in defining value of a service provided by the pharmacy.

The example method that may be performed in conjunction with the pharmacy modeling subsystem 202 may include a retrospective cross-sectional method conducted using pharmacy claims data of commercially insured and Medicare patients. The method may involve analyzing claims data from approximately 50,000 different retail pharmacies belonging to the largest pharmacies chains and independent pharmacies in the U.S. However, a different number of retail pharmacies may be selected. A method period, such as an annual basis, e.g., April 2012-March 2013, may be selected.

An example method may use the data sourced from a comparatively large pharmacy benefits management company that provides pharmacy benefits for commercially insured and Medicare patients. The de-identified data may contain information about patients' claim history, enrollment data and demographic information like age, gender and their geographic location (ZIP). De-identified is defined to include data that does not identify a person individually. The data may also include information about retail pharmacies, such as pharmacy type, location, and affiliation to a corporate chain. This data may be merged with location information, e.g., ZIP level US Census data, to obtain socio-economic characteristics of the study population. Other location information can be used in the pharmacy model.

The data may also include more detailed data regarding socio-economic characteristics that may be obtained or derived from third party databases and correlated to the pharmacy data.

The unit of analysis in an example method that may be performed in conjunction with the pharmacy modeling subsystem 202 may be a retail pharmacy. When the analysis is divided into two separate-analyses, the population selection criteria for these analyses may be different.

For GDR example of the model identification method, all the retail pharmacies that had at least one pharmacy claim during the study period may be identified. In some embodiments, pharmacies that are not coded as retail pharmacy may be excluded. For example, the exclusion may include specialty pharmacies, Long Term Care facilities, Veteran Administration Units, Military Treatment Facilities and pharmacies within clinics. It is envisioned that the present disclosure can be adapted to specialty pharmacies by a type of specialty pharmacy, where a type of specialty pharmacy is compared to a same type of specialty pharmacy. From this set, all the pharmacies that had dispensed less than 1000 claims during the study period may be excluded. However, other numbers of claims such as 100, 200, 500, 1500, 2000 or otherwise may be used.

For adherence, all patients who had at least two pharmacy claims for any of the therapy classes of interest (e.g., Antidiabetics, Antihypertensives and Antihyperlipidemia) may be identified. Patients who had a mail order claim or had filled their medications in any of the specialty pharmacies, Long Term Care facilities, Veteran Admin Units, Military Treatment Facilities and pharmacies within clinics may then be excluded from the method. From this list of patients and retail pharmacies, any pharmacy that had less than five patients for the therapy class that was studied may be excluded. However, more or less patients may be used as the threshold exclusion.

A patient or member threshold can be applied in the creation of any pharmacy model or the application of the pharmacy model to a particular pharmacy. The threshold ensures that the there is sufficient data to perform the method 400 to create pharmacy model. The threshold is used in the model as applied to a pharmacy to ensure that the model produces accurate results with regard to a therapy class.

The method may use the residuals (or error terms) obtained from the multivariate statistical models developed for the pharmacy quality measures to measure the 'true' performance of a pharmacy after adjusting for the factors that influence the quality measure.

An example method can be represented as follows:

An expected value ($E_i$) of the quality measure obtained from the multivariate adjusted statistical model for each pharmacy (i). The expected value $E_i$ can be calculated using a model determined from the method 400. Hence the expect value is based on the limited number of factors in the model and not all factors related to the pharmacy. The expected value is based on twenty or fewer factors that are part of a particular model. The model may not be limited to a particular pharmacy and may be used for other pharmacies. The model may, however, be limited to a particular quality measure, e.g., GDR or adherence to a particular drug regimen. An actual value ($A_i$) of the quality measure as computed from the claims information for each pharmacy (i).

Residual of the quality measure at a pharmacy=$A_i - E_i$.

For example, consider a pharmacy A with a GDR of 63%, which means 63% of the prescriptions filled in that pharmacy are generics. After adjusting for factors such as member demographics, plan design, geography and so on, if a determination is made that expected GDR (e.g., using the model from the method 400) at that pharmacy is 60%, then the residual is a positive 3%. The positive 3% residual reflects that pharmacy A is performing better than expected on GDR measure. A similar approach may be used for adherence measures of pharmacy performance as well. Hence, a positive residual is an indication of good performance from a pharmacy and conversely a negative residual means that the pharmacy is not performing to the expectation.

The analysis performed by the method may be split into two sub-analyses in order to study GDR and medication adherence separately. In the first analysis, a multivariate regression model for GDR may be developed, which adjusted for factors that could be beyond the control of a retail pharmacy. Some of these factors include patient demographics, pharmacy benefits or plan factors and geographic location of the pharmacy, which can be selected using the method 400.

Similarly, the second analysis examined medication adherence at a pharmacy controlling for factors that are beyond the control of a retail pharmacy. Since three separate adherence measures are being analyzed, each of the measure may be modeled individually using multivariate statistical model. Proportion of Days Covered (PDC), may be used as the measure of patients' adherence to a medication. A patient with PDC ≥0.8 for the therapy class analyzed may be considered adherent.

The pharmacy modeling subsystem 202 may be used as part of the statistical model development. Pharmacy modeling subsystem 202 may use the method 400 to establish the model to determine pharmacy performance.

The model may be developed separately for the GDR portion relative to medication adherence portion of the method.

Generic Dispensing Rate

Generic Dispensing Rate (GDR) at a pharmacy is generally defined as the proportion of number generic drugs dispensed over total number drugs dispensed during the study period. This ratio may be bounded between 0 and 1. The method may compute this metric for a number of pharmacies in the method (e.g., all pharmacies being studied) along with various other pharmacy, patient, benefit and geographic attributes. The GDR metric may then be used as a dependent variable with other factors as independent factors. A multivariate linear regression model may be developed using $\frac{2}{3}^{rd}$ of the data as training sample and the remaining $\frac{1}{3}^{rd}$ as the validation sample. However, other proportions may also be used.

Table 1 shows a list of variable factors that can be used in a GDR model. The domain indicates an area where the factor can be grouped

TABLE 1

| Variables in Generic Dispensing Ratio (GDR) model | |
|---|---|
| Domain | Variable |
| Demographic & Socioeconomic attributes | Average age of patients % Female patients Average ZIP level household income of patients |
| Pharmacy benefit design attributes | Average Copay for brand drugs dispensed Average Copay for generic drugs dispensed Proportion claims with Prior Authorization |

TABLE 1-continued

| Variables in Generic Dispensing Ratio (GDR) model | |
|---|---|
| Domain | Variable |
| Pharmacy location Therapy class variables, % claims dispensed | US Census Region ADHD Allergy Antianxiety Antibiotics Antidepressants Antifungals Antivirals Asthma & COPD Cough & Cold Dermatological Diabetes Ear, Nose & Throat Hormone Replacement Hypertension Lipid lowering Ophthalmological Urological |

Medication Adherence

Medication adherence for each pharmacy may be modeled at the therapy level. Hence, separate models may be developed for Antidiabetics, Antihypertensives and Antihyperlipidemia. To model these conditions, a proportion of patients who are adherent to their medication for each pharmacy may be computed.

The ratio may be calculated as below (an example for Antidiabetics)

$$\text{Proportion of adherent patients at pharmacy} = \frac{\text{Number of patients taking oral diabetes medication and } PDC \geq 0.8}{\text{Number of patients taking oral diabetes medication}}$$

The metric may be computed for every retail pharmacy in the method along with various other pharmacy, patient, benefit and geographic attributes. The calculated proportion of adherent patients at pharmacy may then be used as a dependent variable with other factors as independent factors. A multivariate linear regression model was developed using $\frac{2}{3}^{rd}$ of the data as training sample and the reaming $\frac{1}{3}^{rd}$ as the validation sample.

Table 2 shows variable factors that can be used in a model to compute adherence.

TABLE 2

| Final list of variables in Adherence models | |
|---|---|
| Domain | Variable |
| Demographic & Socioeconomic attributes | Average age of patients % Female patients Average ZIP level household income of patients |
| Pharmacy benefit design attributes | Average Copay for drugs dispensed for the therapy class studied Average days supply per Rx |
| Pharmacy location | US Census Region |
| Patient characteristics at the pharmacy | Average Chronic Disease Score (CDS) for patients at the pharmacy Percent of patients new to therapy |

TABLE 2-continued

Final list of variables in Adherence models

| Domain | Variable |
| --- | --- |
| Therapy class variables, % claims dispensed | Antibiotics<br>Antidepressants<br>Antifungals<br>Lipid Lowering<br>Narcotics & Pain Relief<br>Thyroid<br>Ulcer and Heartburn |

After development of the statistical models, calculation of the expected performance measures for each pharmacy in a selected sample may be performed. Residual for each quality measure may then be calculated as the difference between actual value of the measure minus the expected value of the measure.

Results for the Medicare Model

Generic Dispensing Rate

In an example embodiment, the final sample size for the Medicare GDR model may be 36,281 pharmacies. The results from the statistical model are provided in Table 3.

TABLE 3

Results from the Medicare GDR model (Dependent variable = GDR)

| Model Covariates | Estimate Parameters | Pr > \|t\| |
| --- | --- | --- |
| Average patient copay for all the generic medications filled at the pharmacy | −0.005 | <.0001 |
| Average ZIP level household income patients filling at the pharmacy | −0.00000023 | <.0001 |
| Proportion of females filling at the pharmacy | −0.00026 | <.0001 |
| Proportion of claims dispensed for Antianxiety | 0.002 | <.0001 |
| Proportion of claims dispensed for Antibiotics | 0.004 | <.0001 |
| Proportion of claims dispensed for Antidepressants | 0.005 | <.0001 |
| Proportion of claims dispensed for Antifungals | 0.007 | <.0001 |
| Proportion of claims dispensed for Antivirals | −0.006 | <.0001 |
| Proportion of claims dispensed for Asthma and COPD | −0.007 | <.0001 |
| Proportion of claims dispensed for Dermatological | −0.005 | <.0001 |
| Proportion of claims dispensed for Ear Nose & Throat | −0.005 | <.0001 |

TABLE 3-continued

Results from the Medicare GDR model (Dependent variable = GDR)

| Model Covariates | Estimate Parameters | Pr > \|t\| |
| --- | --- | --- |
| Proportion of claims dispensed for Hypertension | 0.004 | <.0001 |
| Proportion of claims dispensed for Miscellaneous agents | −0.008 | <.0001 |
| Proportion of claims dispensed for Narcotic Pain Relief | 0.002 | <.0001 |
| Proportion of claims dispensed for Ophthalmological | −0.005 | <.0001 |
| Proportion of claims dispensed for Hormones | 0.006 | <.0001 |
| Proportion of claims dispensed for Select Biotech | −0.005 | <.0001 |
| Proportion of claims dispensed for Thyroid | 0.003 | <.0001 |
| Proportion of claims dispensed for Ulcer and Heartburn | 0.001 | <.0001 |
| Percent of Prior Authorizations (PA) at the pharmacy | −0.009 | <.0001 |
| pharmacy location state is AK | −0.046 | <.0001 |
| pharmacy location state is AZ | 0.008 | <.0001 |
| pharmacy location state is CT | −0.024 | <.0001 |
| pharmacy location state is DC | −0.021 | <.0001 |
| pharmacy location state is DE | −0.022 | <.0001 |
| pharmacy location state is GA | −0.006 | <.0001 |
| pharmacy location state is IA | 0.017 | <.0001 |
| pharmacy location state is IN | −0.011 | <.0001 |
| pharmacy location state is KY | −0.008 | <.0001 |
| pharmacy location state is LA | −0.045 | <.0001 |
| pharmacy location state is MA | 0.030 | <.0001 |
| pharmacy location state is MD | −0.004 | 0.0018 |
| pharmacy location state is MI | 0.026 | <.0001 |
| pharmacy location state is MN | 0.029 | <.0001 |
| pharmacy location state is NC | −0.011 | <.0001 |
| pharmacy location state is NJ | −0.061 | <.0001 |
| pharmacy location state is NM | 0.013 | <.0001 |
| pharmacy location state is NV | 0.010 | <.0001 |
| pharmacy location state is NY | −0.020 | <.0001 |
| pharmacy location state is OH | 0.006 | <.0001 |
| pharmacy location state is OR | 0.014 | <.0001 |
| pharmacy location state is PA | −0.005 | <.0001 |
| pharmacy location state is SC | −0.021 | <.0001 |
| pharmacy location state is TN | −0.005 | <.0001 |
| pharmacy location state is TX | −0.022 | <.0001 |
| pharmacy location state is UT | 0.010 | <.0001 |
| pharmacy location state is WA | 0.012 | <.0001 |
| pharmacy location state is WI | 0.019 | <.0001 |
| pharmacy location state is WV | −0.019 | <.0001 |

Medication Adherence

In an example embodiment, the results from the statistical models developed for medication adherence measures are provided in Table 4.

TABLE 4

Results from the Medicare medication adherence models (Dependent variable = % of Patients with PDC ≥ 80%)

| | Parameter Estimates | | |
| --- | --- | --- | --- |
| Covariates | Diabetes | Hypertension | Lipid Lowering |
| Average age of patients serviced at the pharmacy | 0.26 | 0.64 | 0.43 |
| Average ZIP level household income patients filling at the pharmacy | 0.0000648 | 0.000112 | 0.000153 |
| Average weighted Chronic Disease Score (CDS) at the pharmacy | −0.04 | 0.07 | 0.05 |
| Number of prescriptions per patient for non-antihypertensive medications | 0.25 | — | — |

TABLE 4-continued

Results from the Medicare medication adherence models (Dependent variable = % of Patients with PDC ≥ 80%)

| | Parameter Estimates | | |
|---|---|---|---|
| Covariates | Diabetes | Hypertension | Lipid Lowering |
| Proportion of claims dispensed for Antibiotics | −0.75 | — | −0.54 |
| Proportion of claims dispensed for Anticoagulants and Antiplatelet | −0.28 | — | — |
| Proportion of claims dispensed for Antidepressants | — | 0.76 | 0.63 |
| Proportion of claims dispensed for Antifungals | −1.12 | — | — |
| Proportion of claims dispensed for Lipid lowering | 0.17 | 0.23 | — |
| Proportion of claims dispensed for Narcotic Pain Relief | −0.59 | −0.34 | −0.34 |
| Proportion of claims dispensed for Thyroid | — | 0.57 | 0.45 |
| Proportion of claims dispensed for Ulcer and Heartburn | — | — | 0.3 |
| Proportion of females filling at the pharmacy | −0.04 | −0.08 | −0.1 |
| Percent of patients who are new to therapy for study medication | — | — | −0.06 |
| Pharmacy in an urban area | −2.38 | −2.33 | −2.95 |
| Pharmacy location state is AL | — | — | −1.99 |
| Pharmacy location state is AR | — | — | −1.65 |
| Pharmacy location state is CA | −1.51 | −3.82 | −3.09 |
| Pharmacy location state is DC | −10.08 | — | −10.16 |
| Pharmacy location state is FL | — | −2.47 | −3.32 |
| Pharmacy location state is GA | −2.53 | −4.84 | −5.49 |
| Pharmacy location state is HI | — | — | −4.51 |
| Pharmacy location state is IA | 4.6 | — | 3.78 |
| Pharmacy location state is LA | — | −3.6 | −2.94 |
| Pharmacy location state is MD | — | — | −2.5 |
| Pharmacy location state is ME | — | — | 5.89 |
| Pharmacy location state is MI | — | 2.9 | 2.51 |
| Pharmacy location state is MN | — | 4.78 | 5.13 |
| Pharmacy location state is MO | — | — | 1.3 |
| Pharmacy location state is MS | — | −3.56 | −4.29 |
| Pharmacy location state is MT | — | — | 6.25 |
| Pharmacy location state is NC | — | −1.98 | −4.15 |
| Pharmacy location state is ND | — | — | 7.3 |
| Pharmacy location state is NJ | −1.93 | — | −2.82 |
| Pharmacy location state is NM | — | — | −3.67 |
| Pharmacy location state is NV | −2.04 | — | −2.67 |
| Pharmacy location state is NY | — | — | −0.83 |
| Pharmacy location state is PA | 2.2 | — | — |
| Pharmacy location state is SC | — | −3.34 | −4.69 |
| Pharmacy location state is TN | — | — | −2.11 |
| Pharmacy location state is TX | −2.07 | −4.21 | −3.81 |
| Pharmacy location state is UT | — | −5.81 | −2.9 |
| Pharmacy location state is VA | — | — | −1.99 |
| Pharmacy location state is VT | — | — | 7.77 |
| Pharmacy location state is WA | — | — | 1.4 |
| Pharmacy location state is WI | 4.95 | 4.49 | 4.33 |

The results from both GDR model and medication adherence models in the example show that the factors like demographics, copay information, geography and the therapeutic mix at a pharmacy is statistically correlated to the pharmacy quality measures via the model as determined for a therapy class. Hence, these factors may be considered and adjusted for by the pharmacy modeling subsystem 202 while calculating the performance measures. These factors can be selected using the method 400.

Commercial Population

A similar methodology (as described in the above sections) was used to develop the statistical models for the Commercial population (Employer-sponsored health insurance plans). The tables below provide the results of examples of these analyses.

Results for the Commercial Model

Generic Dispensing Rate

The results from the GDR model show that the factors like demographic, socioeconomic, benefit design, geographic and therapy class variables at a pharmacy are statistically correlated to the pharmacy quality measure (GDR). These factors are to a large extent not under the control of the pharmacies and hence the pharmacies cannot influence their performance by controlling these factors. The final sample size for the GDR model was 47,509 pharmacies. The results from the example statistical model are provided in Table 5.

TABLE 5

Results from the Commercial GDR model (Dependent variable = GDR, n = 47,509)

| Model Covariates | Parameter estimate | P-Value |
|---|---|---|
| Demographic & Socioeconomic attributes of patients serviced at the pharmacy | | |
| Average age of patients | −0.00044842 | P < 0.001 |
| % Female patients | 0.00040943 | P < 0.001 |

TABLE 5-continued

Results from the Commercial GDR model
(Dependent variable = GDR, n = 47,509)

| Model Covariates | Parameter estimate | P-Value |
|---|---|---|
| Average ZIP level household income of patients | −0.000000695141 | P < 0.001 |
| Pharmacy benefit design attributes of patients serviced at the pharmacy | | |
| Average Copay for brand drugs dispensed | 0.0003817 | P < 0.001 |
| Average Copay for generic drugs dispensed | −0.00731 | P < 0.001 |
| % Prior Authorization claims | −0.00284 | P < 10.001 |
| Therapy class variables, % claims dispensed | | |
| ADHD | −0.00263 | P < 0.001 |
| Allergy | 0.00068121 | P < 0.001 |
| Antianxiety | 0.00088845 | P < 0.001 |
| Antibiotics | 0.00292 | P < 0.001 |
| Antidepressants | 0.00242 | P < 0.001 |
| Antifungals | 0.00452 | P < 0.001 |
| Antivirals | −0.00702 | P < 0.001 |
| Asthma & COPD | −0.00612 | P < 0.001 |
| Cough & Cold | 0.00188 | P < 0.001 |
| Dermatological | −0.00301 | P < 0.001 |
| Diabetes | −0.0036 | P < 0.001 |
| Ear, Nose & Throat | −0.00564 | P < 0.001 |
| Hormone Replacement | −0.00971 | P < 0.001 |
| Hypertension | 0.00245 | P < 0.001 |
| Lipid lowering | −0.0028 | P < 0.001 |
| Miscellaneous Agents | −0.00841 | P < 0.001 |
| Ophthalmological | −0.00453 | P < 0.001 |
| Select Biotech | −0.00842 | P < 0.001 |
| Urological | −0.00585 | P < 0.001 |
| Pharmacy location variables, US States | | |
| CT | −0.0298 | P < 0.001 |
| DC | −0.03553 | P < 0.001 |
| DE | −0.04055 | P < 0.001 |
| GA | −0.00922 | P < 0.001 |
| IA | 0.01312 | P < 0.001 |
| ID | 0.02049 | P < 0.001 |
| IN | −0.0179 | P < 0.001 |
| LA | −0.02333 | P < 0.001 |
| MA | 0.05442 | P < 0.001 |
| MD | −0.01635 | P < 0.001 |
| MI | 0.02425 | P < 0.001 |
| MN | 0.04192 | P < 0.001 |
| MS | −0.02101 | P < 0.001 |
| NC | 0.00348 | P < 0.001 |
| NH | 0.02749 | P < 0.001 |
| NJ | −0.08862 | P < 0.001 |
| NM | 0.02618 | P < 0.001 |
| NY | −0.01218 | P < 0.001 |
| OH | −0.00605 | P < 0.001 |
| OK | −0.00997 | P < 0.001 |
| OR | 0.03882 | P < 0.001 |
| PA | −0.01851 | P < 0.001 |
| PR | −0.11549 | P < 0.001 |
| SC | −0.01251 | P < 0.001 |
| TX | −0.02548 | P < 0.001 |
| UT | 0.02104 | P < 0.001 |
| VA | −0.00619 | P < 0.001 |
| WA | 0.03234 | P < 0.001 |
| WI | 0.0161 | P < 0.001 |
| WV | −0.02349 | P < 0.001 |

Medication Adherence

The results from the example statistical models developed for medication adherence measures are provided in Table 6. Similar to the GDR model, the medication adherence model results show that factors like demographic, socioeconomic, patients' disease severity, benefit design, geographic and therapy class variables at a pharmacy are statistically correlated to the quality measure modeled (% of patients' adherent to their medications). For the medication adherence measures, it can be seen that the disease severity indicator (CDS), geographic location of the pharmacy (region) and the concomitant utilization of drugs in other select therapy classes for patients studied at the pharmacy have a statistically significant correlation with the quality measure. When the pharmacy modeling subsystem 202 measures quality at a pharmacy, the pharmacy modeling subsystem 202 may adjust for the factors. The adjustment can be made using the method 400 or be made during calculation when a factor is determined to not have an effect on the outcome or is redundant to another factor.

TABLE 6

Results from the Commercial medication adherence models (Dependent variable = % of adherent patients)

| Model Covariates | Antidiabetics (n = 31,974) | Antihypertensives (n = 29,415) | Antihyperlipidemics (n = 37,872) |
|---|---|---|---|
| Demographic & Socioeconomic attributes of patients serviced at the pharmacy | | | |
| Average age of patients | 0.7648* | 0.74* | 0.89* |
| % Female patients | −0.07* | −0.20* | −0.16* |
| Average ZIP level household income of patients | 0.000116* | 0.000093* | 0.00015* |
| Pharmacy benefit design attributes of patients serviced at the pharmacy | | | |
| Average Copay for drugs dispensed within the therapy class studied | — | −0.105* | −0.08* |
| Average days' supply per Rx | 2.09* | 2.44* | 2.67* |

TABLE 6-continued

Results from the Commercial medication adherence models (Dependent variable = % of adherent patients)

| Model Covariates | Antidiabetics (n = 31,974) | Antihypertensives (n = 29,415) | Antihyperlipidemics (n = 37,872) |
|---|---|---|---|
| Patient characteristics at the pharmacy | | | |
| Average Chronic Disease Score (CDS[1]) for patients at the pharmacy | 0.16* | 0.09* | 0.06* |
| % patients new to therapy for the therapy class modeled | −0.04* | −0.088* | −0.08* |
| Therapy class variables, % claims dispensed for patients studied for the therapy class modeled | | | |
| Antibiotics | −1.10* | — | −0.76* |
| Antidepressants | — | 0.79* | 0.63* |
| Antifungals | −0.96* | −1.85* | — |
| Lipid Lowering | 0.166* | 0.32* | — |
| Narcotics & Pain Relief | −0.33* | −0.15* | −0.15* |
| Thyroid | — | 0.62* | 0.37* |
| Ulcer and Heartburn | — | 0.62* | 0.43* |
| Pharmacy location variables, Urban status /US States | | | |
| Pharmacy located in an urban area indicator[2] | −3.74* | −2.38* | −3.24* |
| AL | — | −1.95* | −1.84* |
| AZ | −3.01* | −4.23* | — |
| CA | −3.74* | −4.59* | −3.22* |
| CO | −5.10* | −5.63* | — |
| DE | — | — | 7.01* |
| FL | −3.83* | −5.79* | −3.55* |
| GA | −4.20* | −5.99* | −3.98* |
| IL | — | — | 2.15* |
| KS | 3.08* | — | 3.35* |
| KY | 13.86* | 3.59* | 10.15* |
| LA | — | −4.03* | −4.50* |
| MI | 4.01* | 3.49* | 3.07* |
| MN | 6.88* | 2.44* | 5.35* |
| MO | — | — | 2.45* |
| MS | — | −4.52* | −4.28* |
| NC | — | −1.86* | −1.10* |
| ND | 12.83* | — | 10.12* |
| NM | — | −3.98* | — |
| NV | −6.25* | −6.06* | −4.16* |
| OH | — | −1.79* | — |
| OK | 4.48* | — | 4.44* |
| PA | 4.26* | 2.13* | 4.52* |
| SC | — | −2.21* | −2.17* |
| TN | — | −2.94* | −1.56* |
| TX | −6.09* | −6.50* | −5.13* |
| UT | −4.33* | −7.78* | −3.02* |
| VA | 2.66* | — | — |
| VT | 11.13* | — | 5.45* |
| WA | — | −1.65* | 1.60* |
| WI | 4.79* | 3.95* | 5.70* |
| WV | 5.75* | — | 3.11* |

Chronic Disease Score is a disease severity or disease burden index.

Core Based Statistical Area (CBSA) provided by US census bureau was used to determine if the pharmacy is located in an urban area.

* Estimates are statistically significant at P <0.001.

Figure 5:
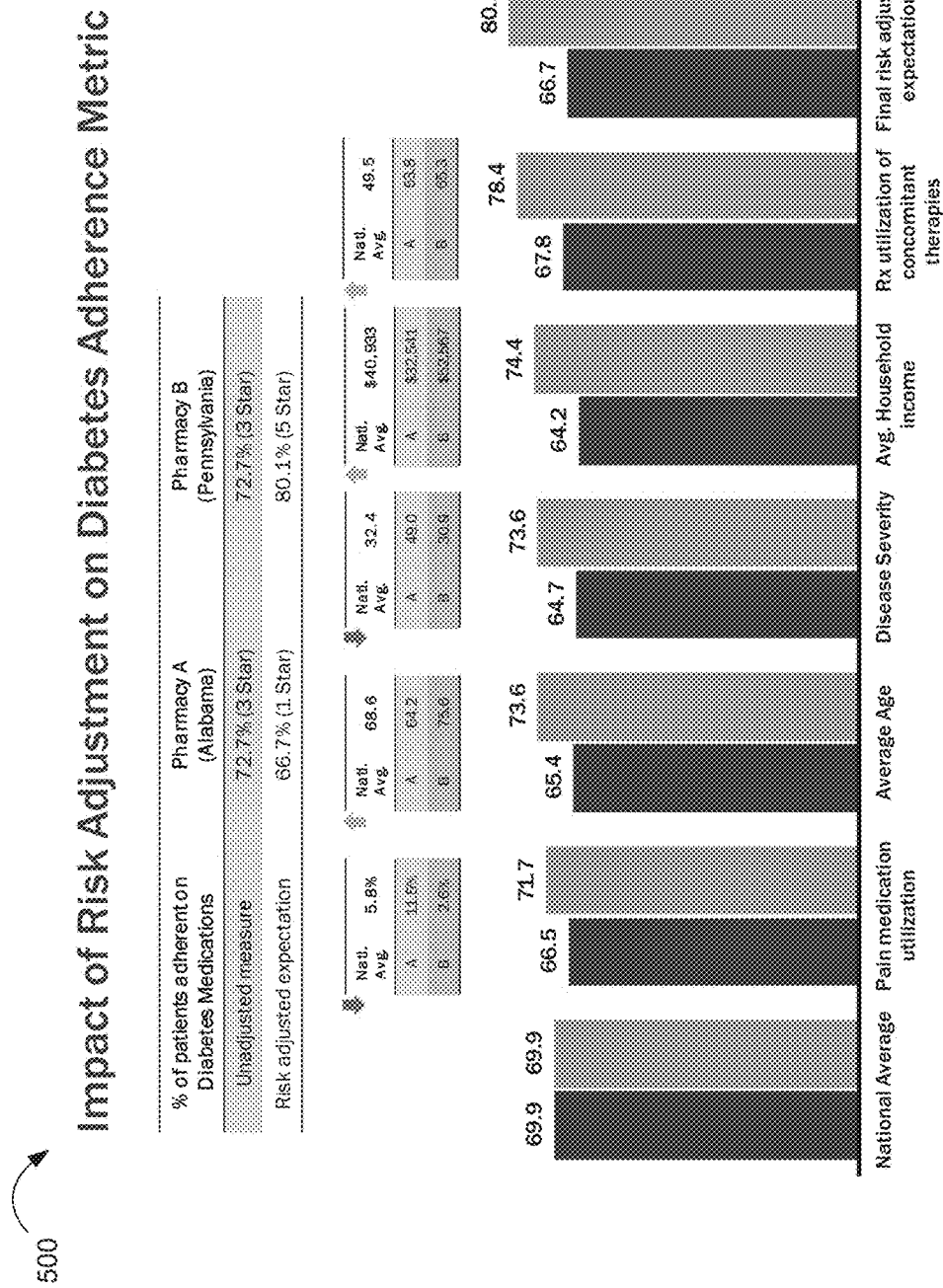
FIG. 5 is an example display, according to an example embodiment.

FIG. 5 is an example display, according to an example embodiment. The display includes a chart 500 that reflects a comparison of the patient populations associated with two pharmacies.

The risk adjustment pharmacy model may be use to determine the standard to which a pharmacy may be held. For example, without associated pharmacy data, the pharmacy may be held to a national adherence average (e.g., that 69.5% of the patients should be adherent or adherence rate).

Analysis may be performed using the pharmacy modeling subsystem 202 to determine 11% of the patients of Pharmacy A are on pain medications, while 2% of the patients of Pharmacy B are on pain medications. In some embodiments, the risk adjustment pharmacy model may reflect that the more patients that a pharmacy has that are taking pain medication the less likely that the patients of the pharmacy are to be adherent. Based on an adjustment determined by the pharmacy model, Pharmacy B should actually be performing at a 71.7% adherence rate and Pharmacy A should be performing at 66.5% adherence rate.

Analysis may be performed using the pharmacy modeling subsystem 202 to determine the average age of the patient population of Pharmacy A and Pharmacy B. The analysis may determine that Pharmacy A has a younger population and that younger people are less adherent (e.g., to prescription drugs). Based on an adjustment determined by the risk adjustment pharmacy model, Pharmacy B should actually be performing at a 73.6% adherence rate and Pharmacy A should be performing at 65.4% adherence rate.

Analysis may be performed using the pharmacy modeling subsystem 202 to determine the disease severity of the patient population of Pharmacy A and Pharmacy B. In some embodiments, the risk adjustment pharmacy model may reflect that patients who are sicker take their medications more regularly because they take their conditions more seriously. Based on an adjustment determined by the risk adjustment pharmacy model, Pharmacy B should actually be performing at a 73.6% adherence rate and Pharmacy A should be performing at 64.7% adherence rate.

Analysis may be performed using the pharmacy modeling subsystem 202 to determine the average household income of the patient population of Pharmacy A and Pharmacy B. In some embodiments, the risk adjustment pharmacy model may reflect that people of lower income are less likely to be adherent. As reflected, the patient population of Pharmacy A has a significantly lower income than the patient population of Pharmacy B. Based on an adjustment determined by the risk adjustment pharmacy model, Pharmacy B should actually be performing at a 74.4% adherence rate and Pharmacy A should be performing at 64.2% adherence rate.

Analysis may be performed using the pharmacy modeling subsystem 202 to determine the prescription drug utilization of concomitant therapies of the patient population of Pharmacy A and Pharmacy B. Based on an adjustment determined by the risk adjustment pharmacy model, Pharmacy B should actually be performing at a 78.4% adherence rate and Pharmacy A should be performing at 67.8% adherence rate.

The various adherence rates may be combined to reflect an 80.1% adherence rate expectation for Pharmacy B versus the 66.7% expectation for Pharmacy A.

Figure 6:
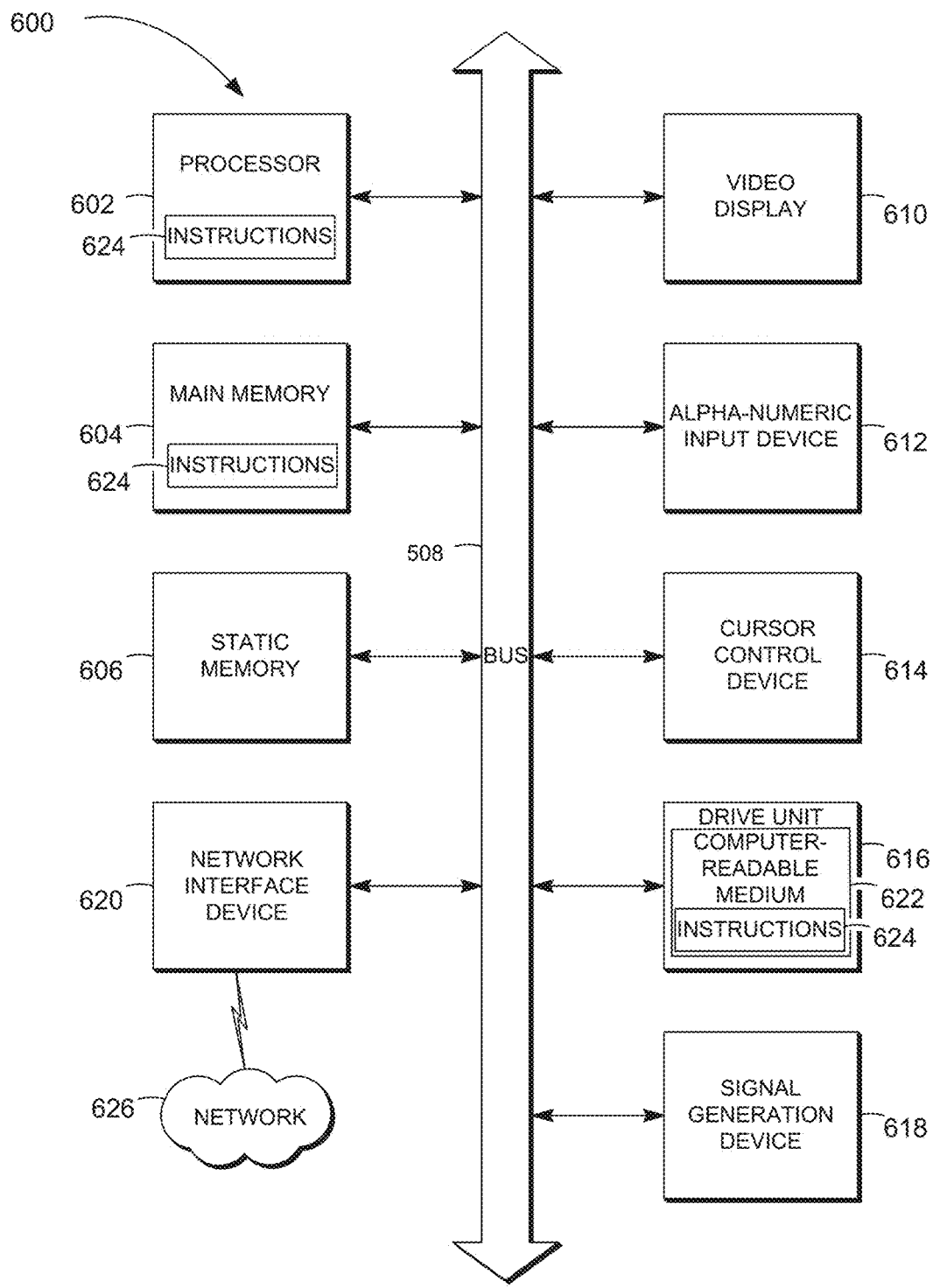
FIG. 6 is a block diagram of a machine in the example form of a computer system within which a set of instructions for causing the machine to perform any one or more of the methodologies discussed herein may be executed or stored.

FIG. 6 shows a block diagram of a machine in the example form of a computer system 600 within which a set of instructions may be executed causing the machine to perform any one or more of the methods, processes, operations, or methodologies discussed herein. The user device 102, the benefit management device 106, and/or the pharmacy device 108 may include the functionality of the one or more computer systems 600.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 600 includes a processor 602 (e.g., a central processing unit (CPU) a graphics processing unit (GPU) or both), a main memory 604 and a static memory 606, which communicate with each other via a bus 608. The computer system 600 further includes a video display unit 610 (e.g., a liquid crystal display (LCD) or a cathode ray tube (CRT)). The computer system 600 also includes an alphanumeric input device 612 (e.g., a keyboard), a cursor control device 614 (e.g., a mouse), a drive unit 616, a signal generation device 618 (e.g., a speaker) and a network interface device 620.

The drive unit 616 includes a computer-readable medium 622 on which is stored one or more sets of instructions (e.g., software 624) embodying any one or more of the methodologies or functions described herein. The software 624 may also reside, completely or at least partially, within the main memory 604 and/or within the processor 602 during execution thereof by the computer system 600, the main memory 604 and the processor 602 also constituting computer-readable media.

The software 624 may further be transmitted or received over a network 626 via the network interface device 620.

While the computer-readable medium 622 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

Generic Dispensing Rate is described herein as an example of quality pharmacy practices. It will be understood that Generic Dispensing Rate is one example of quality of a pharmacy as it relates to generic drug utilization by a pharmacy. Other models may be used with relation to generic drugs and quality of care of the pharmacy.

A described herein the present processes can be performed on a benefit manager device. The present disclosure is not limited to benefit manager device and includes other devices that have access to the data, e.g., a government oversight device or industry wide device. Such a device will include circuitry that when executing any of the method steps described herein become a dedicated machine executing the present method. It will be understood that such a machine may be adaptable to other methods that may or may not relate to determining pharmacy performance or pharmacy risk.

Measures of pharmacy quality or risk can be defined and measured with some accuracy using pharmacy claims data, such a measure does not adjust for factors that are beyond the control of the pharmacies. The factors can include demographics of patients serviced, plan design factors, prior authorizations and such. Other factors that may be statistically significant for some models in evaluating pharmacy performance or risk include age, gender, geography and patient copay—these can be statistically significant effect on the patient's adherence to a medication. These factors also have an effect on a patient's behavior towards generic drug utilization. Hence, it is important to develop a pharmacy quality measure that control for these factors. The presently described systems and methods provide a methodology to empirically adjust the pharmacy quality measure that adjusts the influence of factors that are beyond the control of individual pharmacies.

The systems and methods described herein can relate particular performance metrics on a pharmacy level to identify a more accurate performance profile of a pharmacy, which can be used to compare a pharmacy's performance with the performance of other pharmacies using the improved rating. This improved rating then can be used as benchmarking data for future performance evaluations. Additionally, training and advise can be based on the improved rating to improve pharmacy performance. Any improvement action plan for a pharmacy is then targeted and customized for that particular pharmacy.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

Thus, methods and systems for pharmacy modeling have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
accessing member data, claims data, and population data;
creating a pharmacy predictive model based on the member data, the claims data, and the population data;
determining a calculated adherence percentage for a therapy class at a pharmacy;
calculating an expected adherence percentage for the therapy class at the pharmacy using the pharmacy predictive model; and
comparing the calculated adherence percentage for the therapy class at the pharmacy to the expected adherence percentage for the therapy class at the pharmacy.

2. The method of claim 1, wherein the therapy class includes at least one of the therapy class for antibiotics, antidepressants, antifungals, lipid lowering, narcotics & pain relief, thyroid, and ulcer and heartburn.

3. The method of claim 1, wherein creating the pharmacy predictive model includes relating the member data to a particular pharmacy for use in creating the pharmacy model, wherein the member data includes demographic attributes of the member.

4. The method of claim 3, wherein creating the pharmacy predictive model includes compiling data based on location of the particular pharmacy.

5. The method of claim 3, wherein creating the pharmacy predictive model includes claims data relating to copay for drugs dispensed in the therapy class.

6. The method of claim 1, wherein creating the pharmacy predictive model includes compiling a first set of factors to possibly relate to adherence at the pharmacy, reducing the first set of factors to a second set of factors that reflect only factors that influence pharmacy performance for adherence in the therapy class and including the second set of factors in the pharmacy predictive model.

7. The method of claim 6, wherein creating the pharmacy predictive model includes assigning a weight to each of the factors in the second set of factors.

8. The method of claim 6, wherein the second set of factors includes an average days supply per prescription factor.

9. The method of claim 6, wherein the second set of factors includes an average chronic disease score for patients at a particular pharmacy factor and a member new to the therapy class factor.

10. The method of claim 1, wherein creating the pharmacy predictive model includes excluding any pharmacy that fails to reach a minimum threshold of members.

11. The method of claim 1, wherein determining a calculated adherence percentage includes members who have at least two pharmacy claims in the therapy class.

12. A method comprising:
accessing member data, claims data, and population data;
determining a calculated generic dispensing ratio for a therapy class at a pharmacy;
calculating an expected generic dispensing ratio for the therapy class at the pharmacy using a pharmacy predictive model; and
comparing the calculated generic dispensing ratio for the therapy class at the pharmacy to the expected generic dispensing ratio percentage for the therapy class at the pharmacy.

13. The method of claim 12, wherein the member data include average age of patients at the pharmacy and a level of income in an area at which the pharmacy is located, and wherein determining includes using pharmacy location to determine the calculated generic dispensing ratio and wherein calculating the expected generic dispensing ratio includes using pharmacy location to calculate the expected generic dispensing ratio.

14. The method of claim 13, wherein the pharmacy predictive model includes a variable of a ratio of the therapy class versus activity at the pharmacy.

15. The method of claim 14, wherein the therapy class is one of includes a variable of ADHD, Allergy, Antianxiety, Antibiotics, Antidepressants, Antifungals, Antivirals, Asthma & COPD, Cough & Cold, Dermatological, Diabetes, Ear, Nose & Throat, Hormone Replacement, Hypertension, Lipid lowering, Ophthalmological and Urological.

16. The method of claim 12, wherein creating the generic dispensing ratio predictive model includes compiling a first set of factors to possibly relate to generic dispensing ratio at the pharmacy, reducing the first set of factors to a second set of factors that reflect only factors that influence pharmacy performance for generic dispensing ratio in the therapy class and including the second set of factors in the pharmacy predictive model, and wherein the second set of factors includes an average days supply per prescription Rx proportion of claims with prior authorization factor.

17. The method of claim 12, wherein creating the pharmacy predictive model includes compiling a first set of factors to possibly relate to generic dispensing ratio at the pharmacy, reducing the first set of factors to a second set of factors that reflect only factors that influence pharmacy performance for the generic dispensing ratio and including the second set of factors in the risk adjusted pharmacy predictive model.

18. The method of claim 12, wherein creating the pharmacy predictive model includes excluding any pharmacy that fails to reach a minimum threshold of members.

* * * * *